US00PP32553P2

(12) United States Plant Patent
Hansen

(10) Patent No.: US PP32,553 P2
(45) Date of Patent: Dec. 1, 2020

(54) ***BAPTISIA* PLANT NAMED 'VIOLET DUSK'**

(50) Latin Name: ***Baptisia* hybrid**
Varietal Denomination: Violet Dusk

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,016

(22) Filed: Jan. 15, 2020

(51) Int. Cl.
*A01H 5/02* (2018.01)
*A01H 6/54* (2018.01)

(52) U.S. Cl.
USPC ..... Plt./263.1
CPC ..... *A01H 6/54* (2018.05)

(58) Field of Classification Search
USPC ..... Plt./263.1
CPC ..... A01H 6/54
See application file for complete search history.

*Primary Examiner* — Anne Marie Grunberg

(57) ABSTRACT

A new and distinct plant cultivar of hardy herbaceous false indigo plant named *Baptisia* 'Violet Dusk' characterized by lavender violet cream-colored keels. The new plant has a narrow, upright, vase-shaped, multi-stemmed, winter-hardy habit with glaucous medium-green tri-foliate foliage and is suitable for landscaping as a specimen or en masse.

1 Drawing Sheet

Botanical classification: *Baptisia* hybrid.
Cultivar designation: 'Violet Dusk'.

STATEMENT REGARDING PRIOR DISCLOSURES UNDER 37 CFR 1.77(b)(6)

The first enabling disclosure of 'Violet Dusk', in the form of a sale, was made by Walters Gardens, Inc. on May 13, 2019. Prior to this sale, the new plant was promoted on a website operated by Walters Gardens, Inc. on Feb. 1, 2019, followed by the "Walters Gardens 19-20 Catalog" distributed by Walters Gardens, Inc. first on May 29, 2019. Information and plants for this sale and all sales thereafter were obtained from the inventor. No plants of *Baptisia* 'Violet Dusk' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Violet Dusk' and will be referred to hereafter by its cultivar name, 'Violet Dusk'. The new cultivar represents a new false indigo, a hardy herbaceous perennial grown for landscape and cut flower use.

The new invention arose from an ongoing breeding program of the inventor at a nursery in Waseca, Minn. with continued evaluation at a wholesale perennial nursery in Zeeland, Mich. with the specific intention of improving garden worthiness of perennial false indigo plants with a wider variety of flower colors and improved garden habit.

*Baptisia* 'Violet Dusk' was a single seedling selection from a cross between a proprietary unreleased hybrid selection of *Baptisia alba* times *Baptisia sphaerocarpa* (not patented) as the female or seed parent times a proprietary unreleased hybrid selection of *Baptisia minor* times *Baptisia*

*australis* as the male or pollen parent. Seeds were collected from the individual selected female plant in fall of 2009 at the isolation block in Waseca, Minn., USA by the inventor. The seeds were sown by the inventor at a wholesale perennial nursery in Zeeland, Mich. in the fall of 2009 and the initial selection made in the spring of 2011 at the same nursery in Zeeland and given the breeder code H9-29-5.

'Violet Dusk' was initially asexually propagated by stem cuttings at a nursery in Waseca, Minn., USA in 2008. The resultant plants have demonstrated that the new plant has remained stable and true to type in successive generations of asexual propagation.

The nearest comparison plants known to the inventor are 'Pink Truffles' U.S. Plant Pat. No. 26,588, 'Pink Lemonade' U.S. Plant Pat. No. 30,669 and 'Lavender Stardust' (not patented). 'Pink Truffles' is much taller in habit with soft pink upper banner and lateral petals and a soft yellow keel. 'Pink Lemonade' is much taller in habit and the flowers are light yellow developing a blushing of raspberry-purple. 'Lavender Stardust' has a similar habit, but the flowers have a soft yellow keel to go with the dusty lavender banner. Compared with typical *Baptisia australis* the flowers on the new plant have a more reddish hue and the habit is much smaller. Compared with *Baptisia minor* the new plant is taller in habit and have bluish flowers. Typical *Baptista alba* develop into taller plants with white flowers. Typical *Baptisia sphaerocarpa* has yellow flowers and more open habit. The female parent has yellow flowers on taller plants. The male parent has similar height, but the flowers are vibrant indigo-blue.

The new plant differs from all *Baptisia* known to the inventor in the following combined traits:

1. Lavender violet flowers with cream-colored keels on long spikes.
2. Flowering begins about mid to late spring and continues for about two weeks.
3. Narrow, upright, vase-shaped, multi-stemmed, winter-hardy habit.
4. Glaucous, medium-green, tri-foliate foliage.

BREF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a eight-year-old plant growing in an open full-sun trial garden in Zeeland, Mich.

DETAILED BOTANICAL DESCRIPTION OF THE PLANT

Figure 1:
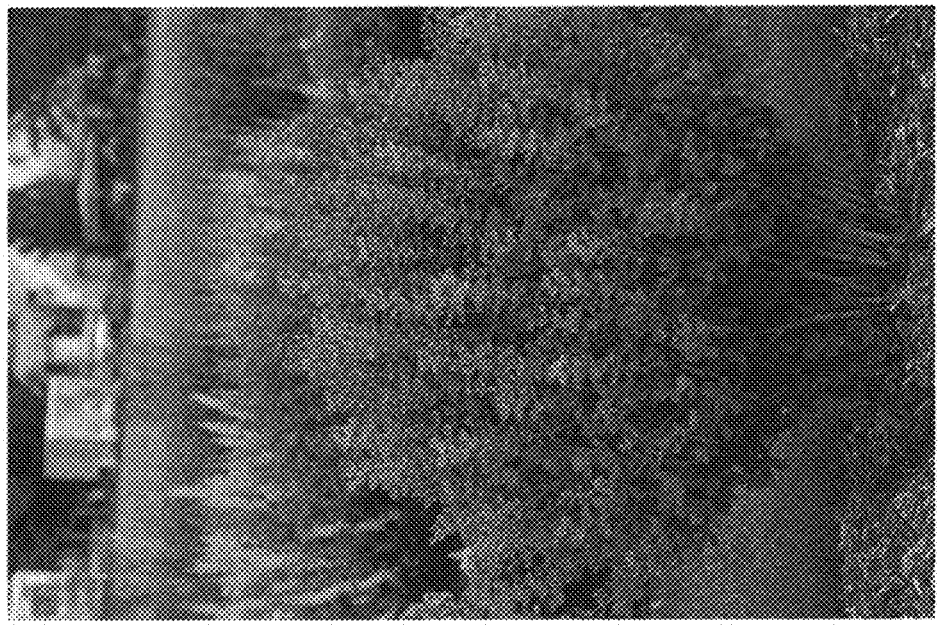
FIG. 1 shows the habit of a plant in full flower.
Figure 2:
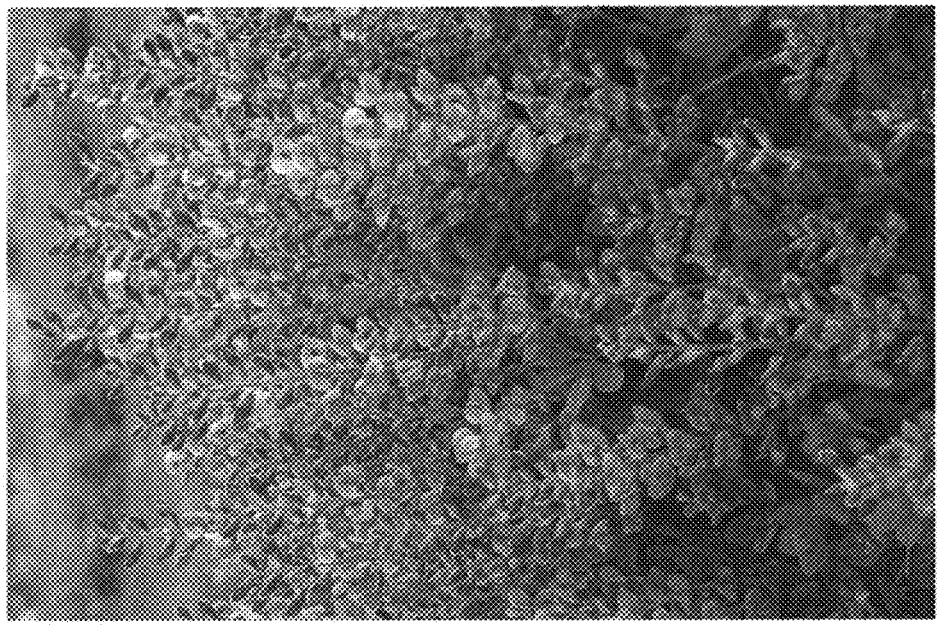
FIG. 2 shows a close-up of the flower scape.

The following is a detailed description of two-year-old plants of the new cultivar as grown outdoors in a production field at a wholesale nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage;

Plant size: Stems and crown about 6 cm across at soil level, about 90 cm tall from soil to top of flowers and 35 cm wide just below initial flowers; at maturity plant height would be about 105 cm tall and about 105 cm wide;

Roots: Fibrous, well-branched, long, deeply rooted;

Root color: Nearest RHS 161D;

Propagation method: Stem cuttings, rooting in about three weeks; also can be propagated successfully by sterile plant tissue culture.

Growth rate: Moderate to slow;

Stems: Rigid and upright to outwardly; highly glaucous; glabrous; cylindrical with longitudinal furrows; lower two to three nodes without leaves or branches; normally two to three stems per plant; main stem to about 8.0 mm diameter at base and 90 cm tall to top of inflorescence, average about 85 cm long and about 7.0 mm diameter; normally about four alternately-arranged primary branches at 55 to 65 degree angle above horizontal, up to 25.0 cm long and 5.0 mm diameter, average for primary branches about 14.0 cm long and 4.0 mm diameter, smaller distally; and three alternately-arranged secondary branches per stem of about 11 cm long and 3.0 mm diameter, averaging about 12.0 cm long and 3.5 mm diameter; normally four alternately-arranged tertiary branches up to 10.0 cm long and 3.0 mm diameter, average about 8.0 cm long and 2.0 mm diameter;

Stem color: Base nearest RHS N138A without glaucous bloom and slightly more green than RHS 122D with glaucous bloom;

Stem scales: At stem nodes; slightly glaucous; dehiscing to leave behind thin scar; about 4.4 cm long and 18 mm wide at base and 23 mm wide in center; frequently with apical three leaflets about 4.0 mm long and 2.0 mm wide in center of retuse apex with sharply pointed sides; truncate base;

Stem scale color: Between RHS 138C and RHS 138B before dehiscing and nearest RHS N200A after dehiscing;

Internodes: Up to 10.0 cm apart between lowest branches, average about 6.0 cm;

Foliage: Alternate on stem; ternate to palmately compound with three leaflets; outer two leaflets independent, at about 90 degree angle to middle leaflet; up to 4.2 cm long and 7.5 cm wide;

Leaflet: Three; obovate; apex acute, base cuneate; margins entire; petiolate; adaxial and abaxial surfaces matte, glabrous; slightly glaucous adaxial and glaucous abaxial; middle lobe to about 37 mm long and 17 mm wide, side lobes about 37 mm long and 17 mm wide;

Leaflet color: Newly expanding nearest RHS 144A on adaxial and abaxial surfaces; mature adaxial nearest RHS NN137C and mature abaxial nearest RHS N138C;

Venation: Pinnate, glabrous, thin, not conspicuous;

Vein color: Newly expanding foliage midrib nearest RHS N144D above and nearest RHS 145D below; main center vein nearest RHS 139D above and lighter than RHS 142D or RHS 145D below; secondary veins same color as surrounding leaf tissue;

Petioles: Glabrous; slightly glaucous; concaved facing upward; up to about 3 mm long and 1.5 mm wide, average 2.0 cm long and 1.5 mm wide;

Petiole color: On expanding leaves nearest 146D, on mature leaves nearest RHS 146A;

Stipules: Narrowly lanceolate, acute apex with base truncate to stem; up to 2.5 cm long and 12 mm wide, average 2.0 cm long and 10.0 mm wide with largest stipules below primary branches and decreasing distally and on secondary branches;

Stipule color: Nearest RHS 138A both surfaces;

Flower: Zygomorphic, papilionaceous, non-secund, held at about 30 degree angle above horizontal; about 45 flowers per main raceme and about 11 per secondary branch; seasonally effective for about 3 to 4 weeks beginning in early to mid-June in Zeeland, Mich.; individual flower remain effective and on raceme for about four days; individually about 24 mm long, 14 mm tall and 14 mm wide at tallest and widest portions; an upper banner, a lower keel made up of two lobes folded around gynoecium and androecium; and two lateral wings or alae laterally appressed against keel;

Flower fragrance: None detected;

Peduncle: Rounded with vertical ridges and furrows; glaucous; glabrous; from first flower to apex about 28 cm long; diameter at the base of first flower about 6.5 mm and about 2 mm diameter at the apex;

Peduncle color: Nearest RHS N187B in flowering portions;

Pedicel: Cylindrical, glabrous, glaucous; about 6.0 mm long and 1.0 mm diameter;

Pedicel color: Ventrally nearest RHS 146D, dorsally nearest RHS;

Calyx: Campanulate; four-lobed; 9 mm long and 7 mm across at apex;

Sepals: Four; one dorsal, one ventral and two lower lateral; acute apices; fused into tube in proximal 6 mm; margin entire; glabrous adaxial and abaxial; dorsal sepal 5 mm wide a fusion; other three sepals 3 mm across at fusion;

Sepal color: Adaxial nearest RHS 146D; abaxial variable with nearest RHS N189B on dorsal side and nearest RHS 147C on the ventral side;

Buds one day prior to anthesis: Oblong elliptic, flatted vertically; about 21 mm long and 8.0 mm tall and 9.0 mm wide;

Bud color: One day prior to opening exposed keel petal blend between RHS 160C and RHS 4D, enfolded banner petal nearest RHS 86D, exposed alae petals nearest RHS 86A;

Petals: Five; with a lower fused keel, an upper banner, and two lateral wings or alae; keel comprised of two sections that are folded around stamens and pistil;

*Banner petal*.—Conduplicate, curved upward and backward and pinched in the middle; apex retuse, base claw-like, margin entire; about 16 mm long, 13 mm across at widest and 7 mm tall.

*Banner color*.—Dorsal side color nearest RHS 86C toward margins with veins nearest RHS 86A, center between RHS N187A and RHS N92A, base nearest RHS 145C; ventral side between RHS 86B and RHS 86C toward margin, center nearest RHS 86A and base nearest RHS 145D; remaining unchanged with maturity.

*Keel*.—Comprised of two main lobes that are folded around stamens and pistil; fused in the distal one-third with the apex emarginate or retuse and the bases separate and claw-like; margin entire; top edge about one-third of the way from base has 2.0 mm smaller lobe pointing toward base; about 20 mm long 4 mm across and 7.0 mm tall with claw base narrowed to 1.0 mm wide for the proximal 3.0 mm.

*Keel color*.—Abaxial keel sides nearest RHS 145D dorsally, base nearest RHS 145C with slight blush of nearest RHS N187A, and nearest RHS 145C ventrally with a strong blush of nearest RHS N187A distally; adaxial base nearest RHS 145D, ventrally nearest RHS 157A and ventrally nearest RHS 157D; remaining unchanged with maturity.

*Alae*.—Two; papilionaceous corolla appendage with rounded apex and claw-like base; with 2.0 mm lobe pointing toward base and about one-third of the way from base; about 21 mm long and 8.0 mm tall with the claw narrowed to 2.0 mm wide for the distal 5.0 mm.

*Alae color*.—Adaxial claw base nearest RHS 145C; main portion nearest RHS 86A, small lobe and region between claw and main portion nearest RHS NN155A; abaxial claw base nearest RHS 145D, small lobe nearest RHS NN155A and main portion nearest RHS 86A; remaining unchanged with maturity.

Receptacle: Disk-shaped, about 4 mm diameter and 1.2 mm depth; color nearest RHS 139A;

Gynoecium: One, with superior ovary and stipe;

*Pistil*.—About 15 mm long and 1.5 mm wide.

*Style*.—Curved at tip, about 6.0 mm long and less than 1.0 mm diameter; color nearest RHS 145A.

*Stigma*.—Less than 0.5 mm diameter; color nearest RHS 145A.

*Ovary*.—Superior suspended by stipe; about 8 mm long and about 1.5 mm in diameter; color nearest RHS 144A.

*Stipe*.—About 5 mm long and 1 mm diameter; color nearest RHS 145A.

Androecium:

*Stamens*.—Ten; cylindrical; glabrous; slightly lustrous; not united, about 21 mm long and 1 mm diameter; color nearest RHS 145D.

*Filament*.—20 mm in length and about 1 mm in diameter; slightly curved upward distally; filament color nearest RHS 145D.

*Anther*.—Dorsifixed, oblong; about 1.5 mm long and 1 mm wide; color nearest RHS 94B.

*Pollen*.—Spherical; abundant; color nearest RHS 17A.

Fruit: Bivalve inflated pod; glabrous; about 25 mm long, 8 mm across and 6 mm thick; with thin, linear, arcuate, terminal beak about 7 mm long and about 1 mm thick;

Fruit color: At maturity nearest N200A;

Seeds: About 11 per flower (open pollinated); reniform; glabrous; about 4.0 mm long, 2.5 mm across and 1.5 mm thick; color between RHS 165A and RHS 165B;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed;

It is claimed:

1. A new and distinct cultivar of hardy False Indigo plant *Baptisia* plant named 'Violet Dusk' as herein described and illustrated.

* * * * *